(12) United States Patent
    Thorell

(10) Patent No.: US 10,292,636 B2
(45) Date of Patent: May 21, 2019

(54) DEVICE FOR USE IN THE EVALUATION OF SUICIDE RISK

(71) Applicant: Emotra AB, Sävedalen (SE)

(72) Inventor: Lars-Håkan Thorell, Linköping (SE)

(73) Assignee: EMOTRA AB, Sävedalen (SE)

(*) Notice: Subject to any disclaimer, the term of this patent is extended or adjusted under 35 U.S.C. 154(b) by 334 days.

(21) Appl. No.: 15/024,908

(22) PCT Filed: Sep. 16, 2014

(86) PCT No.: PCT/SE2014/000115
    § 371 (c)(1),
    (2) Date: Mar. 25, 2016

(87) PCT Pub. No.: WO2015/047147
    PCT Pub. Date: Apr. 2, 2015

(65) Prior Publication Data
    US 2016/0213297 A1    Jul. 28, 2016

(30) Foreign Application Priority Data
    Sep. 25, 2013  (SE) ....................... 1300614

(51) Int. Cl.
    *A61B 5/00*    (2006.01)
    *A61B 5/16*    (2006.01)
    (Continued)

(52) U.S. Cl.
    CPC ............ *A61B 5/165* (2013.01); *A61B 5/0205* (2013.01); *A61B 5/0261* (2013.01);
    (Continued)

(58) Field of Classification Search
    CPC ... A61B 5/165; A61B 5/02416; A61B 5/1123; A61B 5/681
    See application file for complete search history.

(56) References Cited

U.S. PATENT DOCUMENTS

2003/0149344 A1    8/2003  Nizan
2008/0081963 A1    4/2008  Naghavi et al.
(Continued)

FOREIGN PATENT DOCUMENTS

CA          2709670 A1      2/2012
WO     WO-2006/021820      3/2006

OTHER PUBLICATIONS

PCT/ISA/210—International Search Report—dated Feb. 5, 2015 (Issued in Application No. PCT/SE2014/000115).
(Continued)

*Primary Examiner* — Michael J D Abreu
(74) *Attorney, Agent, or Firm* — Jeffri A. Kaminski; Venable LLP

(57) ABSTRACT

A device for evaluation of suicide risk of a person. A measuring unit measures electrodermal activity in fingers of the person to detect depressed persons who are at risk for suicide. The measuring unit is arranged to transmit a sound signal or tone to the person and to provide a signal for analysis of the electrodermal activity from the person. A measuring module measures orientation reactions in the form of blood volume variations of the person, preferably by a phtophletysmographic method peripherally in the fingers and/or centrally in the frontal lobe of the brain through the forehead, and changes in the pulse rate of the test person.

19 Claims, 3 Drawing Sheets

(51) Int. Cl.
| | |
|---|---|
| A61B 5/053 | (2006.01) |
| A61B 5/0205 | (2006.01) |
| A61B 5/026 | (2006.01) |
| A61B 5/0295 | (2006.01) |
| A61B 7/04 | (2006.01) |
| A61B 5/0245 | (2006.01) |
| A61B 5/0456 | (2006.01) |

(52) U.S. Cl.
CPC .......... *A61B 5/0295* (2013.01); *A61B 5/0533* (2013.01); *A61B 5/6803* (2013.01); *A61B 7/04* (2013.01); *A61B 5/0245* (2013.01); *A61B 5/0456* (2013.01); *A61B 5/7203* (2013.01); *A61B 2560/0247* (2013.01); *A61B 2562/0209* (2013.01)

(56) References Cited

U.S. PATENT DOCUMENTS

| | | | |
|---|---|---|---|
| 2008/0214903 | A1 | 9/2008 | Orbach |
| 2008/0255949 | A1 | 10/2008 | Genco et al. |
| 2011/0004072 | A1 | 1/2011 | Fletcher et al. |
| 2011/0245633 | A1 | 10/2011 | Goldberg et al. |
| 2012/0116176 | A1 | 5/2012 | Moravec et al. |
| 2013/0060098 | A1 | 3/2013 | Thomsen et al. |
| 2013/0066395 | A1* | 3/2013 | Simon ............... A61N 2/006 607/48 |
| 2013/0183646 | A1 | 7/2013 | Lusted et al. |
| 2014/0336473 | A1* | 11/2014 | Greco ............... A61B 5/486 600/301 |
| 2015/0077245 | A1* | 3/2015 | Kaufman ........... G06F 19/3418 340/539.12 |

OTHER PUBLICATIONS

PCT/ISA/237—Written Opinion of the International Searching Authority—dated Feb. 5, 2015 (Issued in Application No. PCT/SE2014/000115).

Thorell; "Valid electrodermal hyporeactivity for depressive suicidal propensity offers links to cognitive theory", Acta Psychiatrica Scandinavica, 2009, vol. 119, nr. 5, pp. 338-349.
Thorell; "Electrodermal activity in suicidal and nonsuicidal depressive patients and in matched healthy subjects", Acta Psychiatrica Scandinavica, 1987, vol. 76, nr. 4, pp. 420-430.
Thorell et al; "Electrodermal activity in depressive patients in remission and in matched healthy subjects", Acta Psychiatrica Scandinavica, 1988, vol. 78, pp. 247-253.
Hrabal et al; "Physiological Effects of Delayed System Response Time on Skin Conductance", Multimodal Pattern Recognition of Social Signals in Human-Computer-Interaction, 2012, vol. 7742, pp. 52-62; part "2 Methods".
Zhai et al; "Realization of Stress Detection using Psychophysiological Signals for Improvement of Human-Computer Interactions", Southeast Con. Proceedings IEEE Ft. Lauderdale, FL, 2005, pp. 415-240; part "2 .Physiological aspects of stress detection".
Koelstra et al; "DEAP: A Database for Emotion Analysis Using Physiological Signals", IEEE Transactions on Affective Computing, 2012, vol. 3, nr. 1, pp. 18-21; part "EEG and peripheral physiological features".
Kim et al; "Interactive emotional content communications systems using portable wireless biofeedback device", IEEE Transactions on Consumer Electronics, 2011, vol. 57, nr.4, pp. 1929-1936; part "Overview of the proposed system".
Keltikangas-Jarvinen et al; "Insulin resistance syndrome and autonomically mediated physiological responses to experimentally induced mental stress in adolescent boys", Metabolism, Clinical and Experimental, 1996, vol. 45, nr.5, pp. 614-621; part "Physiological variables".
Sokhadze; "Effects of Music on the Recovery of Autonomic and Electrocortical Activity After Stress Induced by Aversive Visual Stimuli"; Appl Psychophysiol Biofeedback (2007) 32; pp. 31-50; Published online: Feb. 28, 2007; DOI 10.1007/s10484-007-9033-y.
Supplementary European Search Report in corresponding European Patent Application No. EP 14 84 7035 dated Apr. 13, 2017.

* cited by examiner

DEVICE FOR USE IN THE EVALUATION OF SUICIDE RISK

CROSS-REFERENCE TO RELATED APPLICATIONS

The application claims priority to Swedish patent application 1300614-3 filed 25 Sep. 2013 and is the national phase under 35 U.S.C. § 371 of PCT/SE2014/000115 filed 16 Sep. 2014.

FIELD OF THE INVENTION

The present invention relates to a device to be used as a support in the evaluation of suicide risk of a person. The device measures biological signals from the brain of a person in order to detect depressed persons who are at risk for suicide. The device comprises a measuring unit that measures the electrodermal activity in the fingers of the person in order to detect depressed persons who are at risk for suicide. The measuring unit is arranged to transmit a certain experimentally well defined sound or tone signal to the person and to provide a signal for the analysis of the electrodermal response from the person in question.

BACKGROUND OF THE INVENTION

For people aged 15-45 years old suicide is the most common cause of death in industrial countries in the world. One million people commit suicide every year in the world. In Sweden four persons take their lives every day and another 40-60 persons try to take their lives every day.

In Sweden as in other countries, it has traditionally been very difficult to identify those depressed patients who really constitute a risk group for suicide. The only method that has been available so far in traditional health care to identify whether there is a suicide risk has been based on personal interviews by a psychiatrist or other available health care professional and the patients own response to certain standard forms. Such methods are characterized by being fairly subjective. The outcome of such investigations depends on the experience of the health care professional and the way of valuing the interview answers from the patients and therefore tend to be rather arbitrary. The reliability also suffers from the fact that suicidal patients sometimes deliberately withhold suicide plans for the health care professional in order to remove any obstacles to the planned suicide. For example, it has been found that almost 80% of inpatients who take their lives denies such plans in the last week before their suicide.

It has previously been demonstrated by the research of associate professor Lars-Håkan Thorell that there is a strong relationship between the so-called hyporeactivity and suicidal tendencies, while it also has been shown that there is a corresponding strong relation between normal reactivity and "non-suicidal tendencies". It has been shown that the degree of hyporeactivity can be measured objectively and quantitatively by a particular test procedure developed by Lars-Håkan Thorell.

Based on the research developed by associate professor Lars-Håkan Thorell for 25 years, the company Emotra AB, since its start 2001, has developed such a clinically useful and entirely objective method that can be used as a support in the clinical evaluation of suicide risk among depressed patients. The method is based on the use of the so-called EDR tests (Electro Dermal Reactivity), in which tests the ability of the skin (derma) to lead a weak current is utilized, and which has led to the so-called EDOR test (Electro Dermal Orientation Reactivity). The measurements performed according to the EDOR test include among other things electro dermal effects based on the ability of the skin to lead a weak current via the fingertips. The more a person is responding with attention in his brain on a signal, the more sweat glands are activated. The channels of the sweat glands are filled to the skin surface, thus forming more current paths through the skin which in itself has a high electrical resistance so that a larger current is measured.

By testing the response of the patients to certain experimentally well defined sound signals or tones, it has been possible to identify those patients who are so-called electrodermal hyporeactive, i.e. persons who do not show interest in the tones. By definition, hyporeactive persons react very little on signals which is rare among healthy individuals or depressed persons who are not suicidal. However, to react very little to the signals is very common for suicidal depressed patients. A test of this kind will take approximately 15 minutes to complete.

Hyporeactivity implies a strong indication of long-term suicidal propensity among depressed individuals. Once it has been established that a person is hyporeactive, it can be assumed that this state lasts at least 1-2 years. In combination with a severe depression an observed hyporeactivity involves a significant risk for suicide. The method does not claim to replace traditional psychiatric examinations, but is best suited as a supporting complement to the traditional methods. The objectively measured values then gives valuable information about the extent to which the tested person needs treatment, mainly to prevent suicide, but also to treat the depression itself.

The EDOR test measures two different phenomena that differ for people with a hyporeactive dysfunction.

Orientation function—discovered by Pavlov in 1927 and described as "the attention paid to a new event", Habituation of the orientation reaction—was described by Sokolov in 1963 and involves a learning not to unnecessarily react to such events that constitute the normal environment.

Upon exposure of a specific event, persons with a hyporeactive dysfunction show a rather clear pattern of reaction in the form of an often normal orientation reaction to new events, but an extremely fast habituation, i.e. the person finish to care about the event (incident) too soon.

The EDOR test measures the orientation reaction from a well-defined event, a tone. The strength of the reaction is measured as the degree of the changes in the skin conductance and blood flow in the finger tips. Skin conductance is defined as the ability of the skin to lead a small electric current. The skin conductance is measured by providing a current between two electrodes on the finger tips, and the stronger reaction of the patient, the more sweat glands have been activated and the more current is passed through the skin. Furthermore, at a reaction the blood flow through the blood vessels is altered as the vessels constrict. Also the pulse becomes slower and the respiration decreases. By repeating the event, i.e. the tone, the habituation of the orientation reaction can be measured.

In FIG. 3 (below) it is illustrated two typical examples of response to tone stimuli from a reactive and a hyporeactive person, respectively.

The EDOR test itself is not further described here, but it is referred to the studies published by Thorell 2009-2013 as well as to the accompanying literature list.

In WO 02/01478 it is described more generally electrodermal measurements and psychophysiology. This publication describes a small mobile wireless communication system that enables interaction between two or more people so that each one can experience psychophysiological signals, such as visual-, auditory- and/or sensory signals, from one or more of the other interacting persons. This can be possible by means of small, simple and inexpensive electronic solutions and signal codes, as described in the patent publication, and a signal transmitting network, such as Internet or a mobile/telephone network. It is implied in the publication that the system might be used in a "Depression—or suicide research/clinic", but it is not further described how this could be done.

At the EDOR test a special apparatus is used to measure the biological signals from the brain to detect depressed patients who are at risk for suicide. The apparatus comprises a handheld measuring unit with sensor means for measuring electrodermal activity in the fingers of the patients. In addition to the handheld measuring unit the apparatus also comprises headphones and a computer for the analysis of the measurements. The measuring unit transmits an experimentally well defined, specific tone to the patient through the headphones. The tone is repeated according to a specific, tested schedule in widely varying intervals around about 40 seconds. The electrodermal activity of the patient is measured throughout the entire test which takes 15 minutes.

The measuring unit has a size similar to a conventional spectacle case. The measuring unit is placed on the desk in front of the patient/test person. Sensor means in the form of skin conductance electrodes for measuring the electrodermal activity are mounted on the upper side of the measuring unit and on which the patients are allowed to place their fingers during the test.

If the psychiatric health care should be able to rely on a test of this kind, that aims to serve as a routine method for the assessment of suicidal propensity, the test must be very reliable, i.e. the test must have a significant high precision. In order for the test to be sufficiently reliable it must be carried out under almost ideal conditions, so that no external factors are affecting the test and it must be performed in such a way that all the factors/variables that might affect the test result are controlled.

So far it has been difficult to reach ideal conditions and it has not been possible to check all affecting variables. For that reason it has heretofore also been necessary to accept some uncertainties in the interpretation of the measuring result. Such uncertainties might be unacceptable for the mental health care to rely on the test, or alternatively, it requires an extensive and time consuming extra analysis to interpret the results and identify a hyporeactive patient.

Although misinterpretations are rare in the tests it might happen, The reasons for misinterpretations could be that the current test only relies on sound stimuli for the measurement of electrodermal activity. The testing process is thus affected by undesirable interference from the surrounding environment, such as noise interference, which might reduce the precision of the measuring result. Moreover, tremors and other nervous reactions of the patient might adversely affect the testing process. Furthermore, in the existing test procedure there is no possibility to control a number of variables that each one has a particular influence on the interpretation of the measuring result. The weaknesses identified in the existing test increases the demands of skill of the health care professional who interprets the measuring result and the reliability of the interpretation of the measuring result is then somewhat reduced and thus the precision of the test.

It has also been found a small percentage of depressed patients who do not show any reaction at all at the electrodermal measurement and at the same time a very low electrical conductance. In these cases it is supposed that the sudomotorical (sweat) system for some reason has been destroyed, but it might be another reason, that the patient is not at all responsive to the orientation reactions. If the electrodermal system is destroyed but the orientation reactions are existing in the brain, then these reactions can be detected as peripheral blood volume changes (e.g. blood volume decrease in the fingers) and central (blood volume increase in the brain) and a slower pulse rate of the patient. In case no orientation reactions can be detected in the blood volume and pulse rate of the patient this strengthen the suicidal propensity.

It is an object of the present invention to reduce/eliminate source of errors of the kind mentioned above and thus ensuring a higher precision in the analysis of the measuring result and/or facilitate the analysis required for the interpretation of the test result.

SUMMARY OF THE INVENTION

A further object of the invention is to complement the electrodermal measurement by additional parameters intended to facilitate the analysis or increase the precision of the analysis of the test result, specifically to detect peripheral and central blood volume changes of a patient.

According to the invention, in addition to the electrodermal measurement, the orientation reactions are also measured in the form of blood volume variations of the patient by means of a photoplethysmographic method.

The photplethysmographic method might then include measurement of peripheral blood volume variations in the fingers and/or centrally in the frontal lobe of the brain through the forehead of the patient.

According to a preferred embodiment of the invention a specific sound signal or tone is provided by the measuring unit to the test person via headphones. The sound signal or tone is repeated according to a specific, tested schedule in widely varying intervals, for example around about 40 seconds during the measurement of the electrodermal and photophletysmographic activity of the test person.

According to a further preferred embodiment the apparatus comprises one or more microphones to detect sound noise and in which case the microphone signals are transmitted in parallel with the electrodermal response signal to be included into the signal analysis.

BRIEF DESCRIPTION OF THE DRAWINGS

In the following the invention will be described more in detail with reference to the accompanying drawings in which, FIG. 1 schematically illustrates the main components of an apparatus for EDOR test, in which the electrodermal response from the test person is analyzed by using a laptop computer.

DETAILED DESCRIPTION OF EMBODIMENTS OF THE INVENTION

Figure 1:
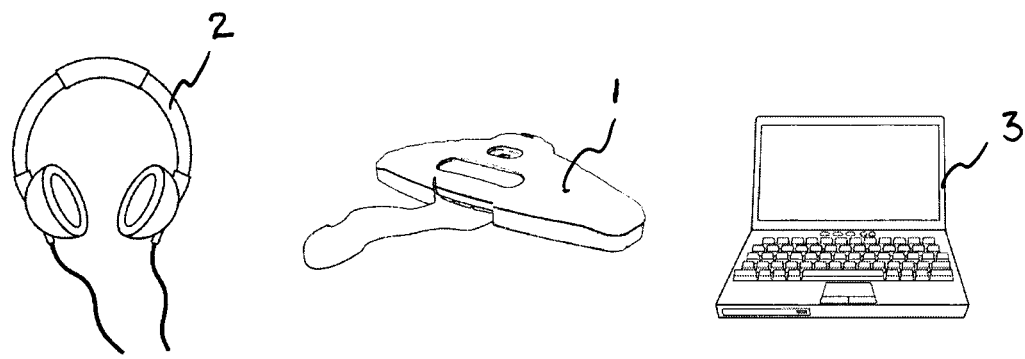
FIG. 1 schematically illustrates the main components of an apparatus for EDOR test of the type which has been described in the introductory portion of our specification. The apparatus thus comprises an easily managed hand held measuring unit 1, a headphone 2 and a laptop computer 3 for the analysis of the electrodermal response from the measuring unit.
Figure 2:
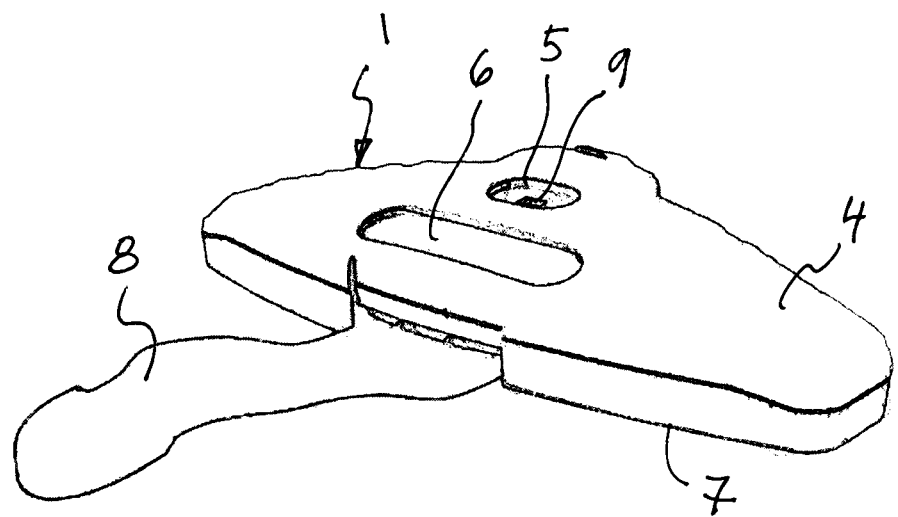
FIG. 2 shows a hand held measuring unit for the EDOR test.

FIG. 2 shows an example of a hand held measuring unit 1 developed by Emotra AB. The measuring unit is designed for easy handling with an upper side 4 with two skin conductance electrodes, a smaller, circular gold electrode 5 and a larger, elongated gold electrode 6, and a bottom side 7 intended to rest against a desk or the like. The measuring unit has a size and shape substantially corresponding to a spectacle case.

As already mentioned the EDOR test is measuring the orientation reactions from a well defined event, in this case a tone. The measuring unit emits via the headphones 2 such an experimentally well defined tone, for instance 1 kHz, 90 dB, 1 second and 10 ms rise and fall times. The tone is repeated according to a specific tested schedule in widely varying ranges around 40 seconds. Following instructions from an authorized test leader the test person puts his index finger tip on the gold electrode 5 and his middle finger on the longer electrode 6. The fingers are held in place by means of an elastic belt 8. The headphones are turned on and the test is started as soon as the test leader concludes that the signal is OK. Throughout the entire test, which takes about 15 minutes, electrodermal and photophletysmographic activities are measured by means of sensors, which are described more in detail below. The strength of the reaction is measured as the size of the changes in skin conductance and blood flow in the finger tips of the patient. The measurement is performed with a pseudo constant DC voltage of 0.5 V across the electrodes 5, 6 powered by a rechargeable battery placed inside the measuring unit.

For measuring the orientation reactions in the form of blood volume variations by means of a photophletysmographic method peripherally in the fingers, photo emitter— and sensor means 9 are placed adjacent to the smaller skin conductance electrode 5 on the upper side 4 of the measuring unit.

Sweat glands are activated and fill their channels to the skin surface and thereby contribute with an additional current component to the electrical circuit through the otherwise high resistant skin. Changes in the measured current across the electrodes is linear and highly related to the change of the number of activated sweat glands. An electrodermal reaction is defined as an increase of the conductance with a minimum criterion for the derivate that occurs after a lower time criterion and a higher time criterion and reaching a minimum criterion for the amplitude. The measuring result is transmitted via wireless Bluetooth technology to the laptop computer 3 for analysis.

Figure 3:
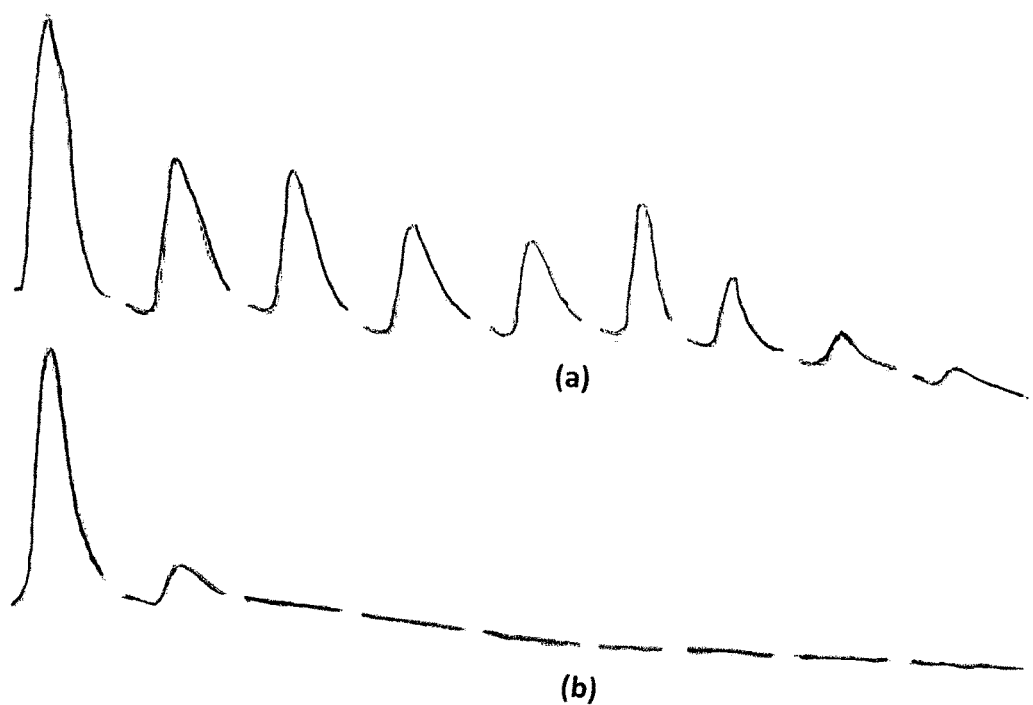
FIG. 3 shows two typical examples of electrodermal response to tone stimuli from a reactive and hyporeactive person, respectively, at an EDOR test.

In FIG. 3 it is illustrated an example of a typical electrodermal response in the form of skin conductance from a tone stimulus for 15 minutes for a reactive as well as a hyporeactive person, curve a and b, respectively. From curve a it is evident that a reactive person learns the normal, while the hyporeactive person ignores the normal (see curve b). The hyporeactive person does not respond to the third and subsequent signals. Habituation is reached already at the third stimulus. The scale of habituation is defined as the sequence number of the first stimulus in a sequence of three that does not cause any electrodermal response.

Figure 4:
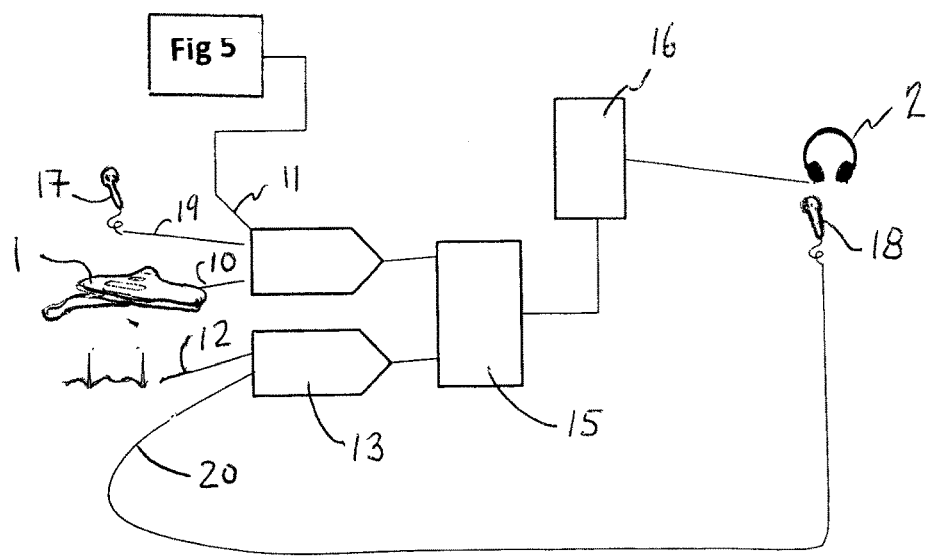
FIG. 4 shows a block diagram of a device according to the invention.
Figure 5:
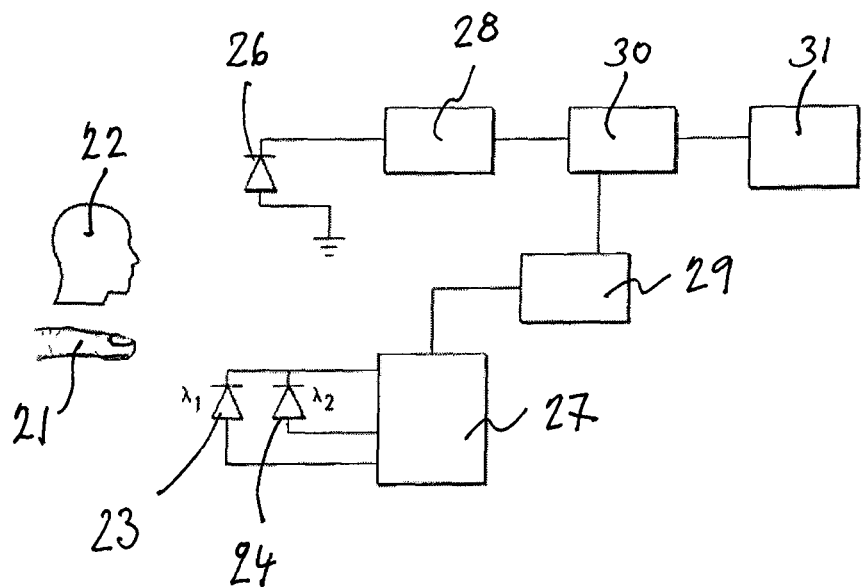
FIG. 5 shows a device for photophletysmography for a device according to the invention.
Figure 6:
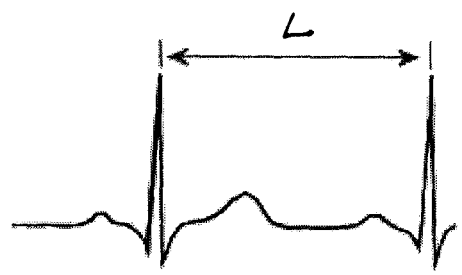
FIG. 6 illustrates how the pulse response of a test person is measured, namely by ranging between two R-waves in an ECG.

In FIG. 4 a block diagram is used to illustrate an example of electronic components in an apparatus according to the invention. Input signals 10 from the electrodermal measuring unit 1 and input signals 11, 12 from the additional photophletysmographic and ECG measurements, see FIGS. 5 and 6, are processed in the electronic circuitry in the apparatus. The signals 10, 11, 12 are supplied to the electronic circuitry by means of A/D converters 13, 14 and micro controls 15, 16 for generating said tone stimulus to the headphones 2. Preferably the apparatus includes further electronic components such as a rechargeable battery, contact means for the headphones and a Bluetooth output for a wireless transmission of the measuring result via Bluetooth technology to the laptop computer 3 for analysis. Such components are known per se and will not be described any further here.

Even if the EDOR method described so far has a significant high precision within the psychiatric and mental health care field, as already mentioned there is a need to further improve and secure the ability of the existing apparatus to make a distinction between patients who are and who are not suicidal. According to the invention the reliability of the apparatus has been secured by reducing the number of disturbing factors that might happen and, if they still happen, take into account such factors in the measurement. Through such measures a more reliable measurement of the peripheral electrodermal orientation reactivity can be achieved by the apparatus.

As the apparatus is intended for use in the field, i.e. in different rooms at hospitals and universities, in the patient's home and other locations, sudden or prolonged noise as well as light interference might occur. Disturbances of this type which might affect the measurements could be:

a. Telephones, computers or the like which have not been switched off.
b. noise from adjacent rooms, from traffic outside the window or from unauthorized persons coming into the room.
c. Things falling down, test leader sneezing, cough, clearing his throat or similar noise.
d. Lights from traffic outside the window, lightning from thunderstorms or similar light interference.

A common feature of all these disorders is the fact that they give rise to unintentional orientation reactions affecting the real orientation reactions from the programmed sound stimuli so that there is an increased risk of false negative orientation reactions and unwanted error results from the test.

For that reason the apparatus according to the invention has been provided with means for detecting this type of noise interference, i.e. means in the form of a microphone 17 placed adjacent to the measuring unit 1 to detect surrounding noise and/or a microphone 18 located on the headband of the headphones and/or located on an arm extending from the headphones against the cheek of the patient for feedback of noise from the headphone, see FIG. 4. The microphone signals 19, 20 are transmitted in parallel with the signals 10, 11, 12 to the host computer in order to be considered in the interpretation of the test results.

In a preferred embodiment of the invention microphones have also been placed in left and right headphone separately to detect audible sound, i.e. sound which reach the eardrums of the test person. Even these microphone signals are transmitted in parallel with the other signals to the host computer for consideration in the evaluation of the test results. The object of this arrangement is to measure the actual sound that the test person is able to hear during the test.

This means that unwanted sound noise can be considered in the subsequent signal analysis. Furthermore, such an arrangement allows a continuous control of the programmed sound stimuli so that it can be verified that the sound stimuli is really obtained in both the headphones and with a correct volume.

To ensure the validity of the apparatus with respect to the measurement of orientation reactivity, particularly hyporeactivity, according to the invention the orientation reactions are measured in different ways. In addition to the peripheral electrodermal measurement which has been described above, as mentioned there is also a photophletysmographic measurement of the orientation reactions. The photophletysmographic measurement can be either peripheral (through the fingers) or central as a change of the vascular activity in the frontal lobe of the brain via the forehead of the test person, or both peripheral and central, see FIG. 5.

Photoplethysmography (PPG) is a non-invasive technique in which light is absorbed, scattered and reflected back in the human tissue. From the skin PPG can detect both cardiovascular and respiratory variations (PPGr). Stable PPG signals for recording blood volume can be made from different measuring points on the human body with varying vascular structures. In addition to a peripheral measurement of blood volume variations in the fingers, see 21 in FIG. 5, then according to this invention also a phletysmographic measurement of the orientation reactions in the form of blood volume variations centrally, i.e. in the frontal lobe of the brain through the forehead of the test person, see 22 in FIG. 5, is made. Two light emitting diodes (LED) 23, 24 with different wave lengths are provided for the peripheral measurement related to the fingers of the test person and a light emitting diode 26 is positioned adjacent to the forehead of the test person for the central measurement. Preferably, the light emitting diode 26 is mounted on an arm from the headband of the headphones, which arm then is extending a suitable distance from the forehead of the test person. By such an arrangement a more reliable evaluation of the orientation reactions can be made and thereby increases the accuracy of the test. The electronic circuitry further comprises a LED driver 27, amplifier 28, control means 29, demodulator 30 and signal processing means 31 which components are known per se.

Frontal lobe photophletysmography is previously known in itself and has been used in other technical fields. For instance it is referred to the article "Combined photophletysmographic monitoring of respiration rate and pulse: a comparison between different measurement sites in spontaneously breathing subjects" in Acta Anaesthesiol Scand 2007; 51:1250-1257. The advantage of a central photophletysmography is that the PPG signal on the forehead gives a good indication of the brain lobes need of blood at increased brain activity in the lobes.

A further way to increase the precision of the apparatus is to introduce a device for measuring the pulse response of the test person. Pulse rate is most accurately measured as based on the interval L between two R-waves in the ECG, as illustrated schematically in FIG. 6. According to the invention a specific diversion of the ECG signal is used in which the potential difference between a small gold electrode placed midway the photo emitter (light emitting diode) and the—sensor on the arm from the headband of the headphones, or alternatively between a gold electrode in connection with the skin on the headphone on the opposite side of the head relative to the measuring unit, and the elongated electrodermal gold electrode on the casing of the measuring unit is measured by means of an ECG amplifier. A device of this kind increases the ability to more safely determine if an orientation reaction or another type of reaction has occurred and thereby increases the precision of the test.

The invention is not limited to the examples which have been shown here but can be varied within the scope of the following claims.

The invention claimed is:

1. A device for use in an evaluation of suicide risk of a person, the device comprising:
 a first measuring unit that measures electrodermal activity in fingers of the person to be evaluated to detect a depressed person who is at risk for suicide, wherein the first measuring unit is configured to emit and transmit a sound signal or tone to the person to be evaluated and to generate an electrodermal response signal for analysis of the electrodermal activity from the person to be evaluated;
 a second measuring unit configured to measure orientation reactions on sound stimuli from said sound signal or tone, the orientation reactions comprising blood volume variations of the person to be evaluated; and
 at least one microphone configured to detect noise interference, wherein microphone signals are transmitted in parallel with the electrodermal response signal to be included in the signal analysis, and
 wherein the sound signal or tone is repeated in a predetermined interval according to a specific schedule.

2. The device according to claim 1, wherein the measurement of the orientation reactions in the form of blood volume variations is made by a photophletysmographic method.

3. The device according to claim 2, wherein the photophletysmographic method comprises a measurement of blood volume variations centrally in the frontal lobe of the brain through a forehead of the person.

4. The device according to claim 3, wherein the second measuring unit configured to measure the orientation reactions by photophletysmography centrally in the frontal lobe of the brain via the forehead comprises light emitting elements and sensor elements arranged adjacent to the forehead of the person.

5. The device according to claim 4, wherein said light emitting elements and sensor elements are placed on an arm extending from the headphones up to a convenient distance from the forehead of the person during the evaluation.

6. The device according to claim 2, wherein the sound signal or tone transmitted by the first measuring unit is repeated according to a schedule in widely varying intervals during the measurement of the electrodermal and photophletysmographic activity of the person.

7. The device according to claim 6, wherein the sound signal or tone transmitted by the first measuring unit is repeated at about 40 seconds.

8. The device according to claim 2, wherein the photophletysmographic method comprises a measurement of blood volume variations peripherally in the fingers of the person.

9. The device according to claim 2, wherein the photophletysmographic method comprises a measurement of blood volume variations peripherally in the fingers and centrally in the frontal lobe of the brain through the forehead of the person.

10. The device according to claim 1, wherein the first measuring unit is configured to emit and transmit said sound signal or tone via headphones.

11. The device according to claim 1, wherein the electrodermal response signal from the first measuring unit is transmitted to be analyzed in a laptop computer.

12. The device according to claim 1, further comprising:
a sensor configured to measure a pulse response from the person.

13. The device according to claim 12, wherein the pulse response is measured as an interval between two R waves in an ECG.

14. The device according to claim 13, wherein the pulse response is measured by an ECG amplifier.

15. The device according to claim 14, wherein said ECG amplifier is arranged to measure a potential difference between an electrode located between a photo emitter and a sensor on the arm extending from a headband of headphones and an elongated electrodermal electrode on an upper side of the first measuring unit.

16. The device according to claim 1, wherein the microphone is located adjacent to an upper side of the first measuring unit.

17. The device according to claim 16, wherein microphones are located in a left part and a right part of headphones separately in order to detect audible sound, and wherein microphone signals are arranged to be sent parallel to the electrodermal response signal to be included in the signal analysis.

18. The device according to claim 1, wherein the microphone is located at least at one of adjacent to headphones or on an arm extending up to a certain distance from a cheek of the person during the evaluation.

19. A method for evaluating suicide risk of a person, the method comprising:
measuring, by a first measuring unit, electrodermal activity in fingers of the person to be evaluated to detect a depressed person who is at risk for suicide;
transmitting, by first measuring unit, a sound signal or tone to the person to be evaluated and generating an electrodermal response signal by a first measuring unit for analysis of the electrodermal activity from the person to be evaluated;
measuring, by a second measuring unit, orientation reactions on sound stimuli from the sound signal or tone, the measuring comprising measuring blood volume variations of the person to be evaluated; and
detecting noise interference by at least one microphone, wherein microphone signals are transmitted in parallel with the electrodermal response signal to be included in the signal analysis,
wherein the sound signal or tone is repeated in a predetermined interval according to a specific schedule.

* * * * *